United States Patent [19]

Dettmann et al.

[11] 4,230,143
[45] Oct. 28, 1980

[54] CONTROL VALVE ARRANGEMENT FOR DENTAL EQUIPMENT

[75] Inventors: Heinrich Dettmann, Niedernhall; Otto Mehrer, Öhringen, both of Fed. Rep. of Germany

[73] Assignee: Bürkert GmbH, Ingelfingen, Fed. Rep. of Germany

[21] Appl. No.: 962,821

[22] Filed: Nov. 22, 1978

[30] Foreign Application Priority Data

Nov. 26, 1977 [DE] Fed. Rep. of Germany ....... 2752938

[51] Int. Cl.³ .............................................. A61C 19/00
[52] U.S. Cl. .................................... 137/270; 137/884; 433/98
[58] Field of Search ................... 32/22; 137/270, 884; 433/98

[56] References Cited

U.S. PATENT DOCUMENTS

| Re. 28,649 | 12/1975 | Austin, Jr. | 32/22 |
| 4,069,587 | 1/1978 | Peralta | 32/22 |
| 4,136,713 | 1/1979 | Humphreys | 137/270 X |

*Primary Examiner*—Gerald A. Michalsky
*Attorney, Agent, or Firm*—Edwin E. Greigg

[57] ABSTRACT

There is provided a control valve arrangement for dental equipment which comprises a plurality of modular type assemblies having at least three functional zones with the modules including inter-connecting passageways and disposed so as to handle a plurality of separately controlled pressurized media. Provision is also made to rotate a particular module about an X axis to modify the operation of that module.

10 Claims, 18 Drawing Figures

CONTROL VALVE ARRANGEMENT FOR DENTAL EQUIPMENT

BACKGROUND OF THE INVENTION

The invention relates to a control valve arrangement for dental equipment, wherein two or more control valve assemblies are combined into a control group disposed between end pieces and forming an entity, wherein the control valve assemblies are clamped together by longitudinal tie rods and have channels for control and supply media made up of channel sections which are joined together, extend in the direction of said control valve assemblies and are provided in the individual control valve assemblies.

These types of devices are employed to control driving, cooling, and rinsing media for the instruments associated with a dental treatment unit. They must contain variously operating control units, e.g. those working as pressure regulators, suction-regulator valves, shutoff valves, check valves, filter units, etc.

Heretofore, devices have been used as dental treatment units consisting of completely differently constructed control units, depending on the different types of special services, and which were interconnected via external conduits. This required a large amount of mounting space and resulted in a high-cost design of the overall system. The many connections between the conduits and the control units offered a correspondingly large number of leak possibilities. However, units of the type mentioned at the start, i.e. in block design, have likewise been known, as exemplified in Accepted West German Specification 21 51 512. In this case, however, the internal designs of the housings of the individual components were different, depending on their different subtasks so that here, too, the manufacture of the different individual components and the storage thereof made everything expensive. Moreover, the dissimilarity of the individual components which was fixed from the start permitted only a single predetermined combination into an overall system.

OBJECT AND SUMMARY OF THE INVENTION

Therefore, the primary object of the invention is to make inexpensive devices of the type mentioned hereinabove which are easy to modify, and to develop the components that make them up in such a way that they form a space-saving low-cost overall system. The solution according to the invention lies in the fact that the various control valve assemblies (I-V) are made up of basic bodies which are identical in the original state and whose front sides to be clamped together with sealing means as separators are identical, and wherein the ports disposed therein are symmetrical to a normal central plane extending in the direction of clamping, that in the interior of each basic body there is provided a cross chamber passing therethrough and having a valve seat whose geometrical axis runs parallel to the direction of clamping and is intersected at right angles by a central geometrical vertical axis of the basic body, a third geometrical axis likewise passing through the point of intersection and extending at right angles to said two axes, and that in the interior of the basic body there are provided six channel sections which run parallel to the third axis, such that four, in pairs, are symmetrical to the vertical axis as well as to the axis of the cross chamber and two are symmetrical only to the vertical axis.

The device according to the invention permits the user to manage with only a small number of outside connections for at least two of the media to be controlled (air, water); in the example described hereinafter with one outside connection for water and two outside connections for air. It also offers the possibility of selectively feeding said supply media to one of the two sides of the valve seat mounted in the cross chamber. It further permits, in the valve assemblies clamped together, the use of basic bodies in a position which is rotated 180° in relation to the adjacent basic bodies, in which position they fit together, without modification, with the adjacent basic bodies. This rotation possibility of the basic bodies is a contributing factor for dispensing with outwardly conducted supply and control diversions. Further, the invention makes advantageous use of the knowledge that to facilitate cost-saving production, the basic bodies of the various valve assemblies are identical in the initial state, although they must be worked over for use in the individual valve assemblies, but the design of the basic bodies permits the user to manage with very simple finishing processes. The channel sections and chambers are disposed in such a way that they can readily be connected by tap holes, while open channels can readily be closed by balls pressed thereinto. A special development of the channel sections consists in the provision of readily removable partition walls therein, so that such an initially closed channel section can easily be transformed into an open passage and can be connected with other such passages in adjacent basic bodies to form a continuous conduit.

The invention will be better understood as well as further objects and advantages thereof become more apparent from the ensuing detailed description of two exemplary embodiments taken in conjunction with the drawing.

DESCRIPTION OF THE PREFERRED EMBODIMENT

Figure 2:
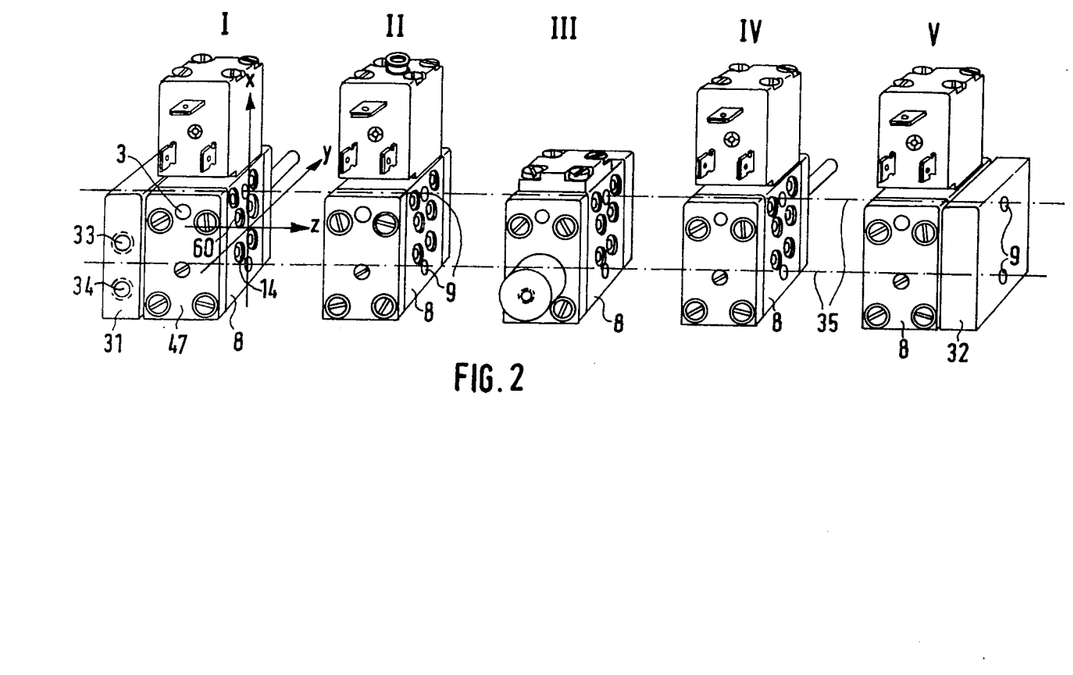
FIG. 2 is an exploded perspective view of the five individual valve assemblies of the device shown in FIG. 1.

Turning now to the example of FIG. 2, water is supplied via conduit 1 and compressed air via conduit 1. These working media must be supplied at controlled pressure separately or simultaneously to junction points for a turbine e.g. a turbine tool holder 3, a spray tool holder 4, a rinsing means 5 and an air-blast nozzle 6, respectively. Control valve assembly I is connected on the inlet side to compressed-air conduit 2 and contains a pressure regulator valve for adjusting the air pressure to a constant operating value and also a 2/2 directional-control valve for supplying the turbine with compressed air. In front of the outlet of the compressed air regulator valve, conduit 7 branches off to control valve assembly II forming a 3/2 directional-control valve and supplying the compressed air for junction point 4 of the spray tool holder.

Control valve block V forming 2/2 directional-control valve is likewise connected on the inlet side to compressed-air conduit 2 and supplies compressed air to junction point 6 for the air-blast nozzle.

To water conduit 1 is connected control valve assembly IV which has a pressure regulator valve and also a b 2/2 directional-control valve for junction point 5 of the rinsing means. To the outlet of the pressure regulator valve of said control valve assembly IV is connected control valve assembly III which is pilot-operated by the outlet of control valve II. Control valve assembly III supplies the water for the spray tool holder 4.

Figure 3:
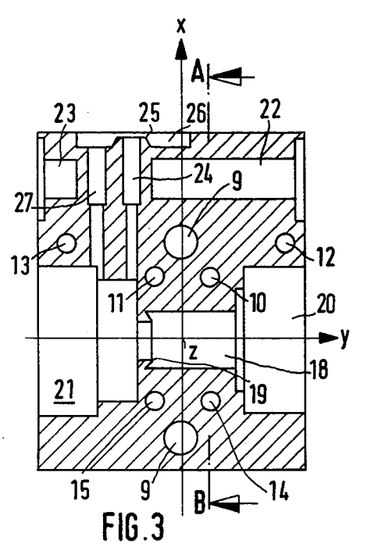
FIG. 3 is a cross-sectional view of a basic body of a control valve assembly.
Figure 4:
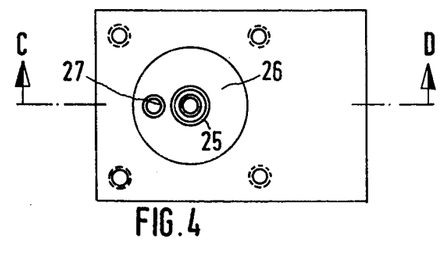
FIG. 4 is a top plan view of FIG. 3.
Figure 5:
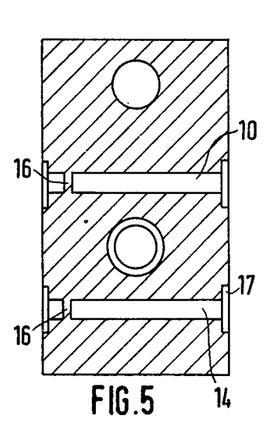
FIG. 5 is a cross sectional view taken along the line A-B in FIG. 3.
Figure 6:
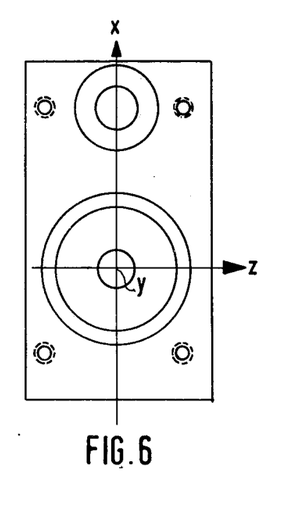
FIG. 6 is a view taken along the line C-D in FIG. 4.
Figure 7:
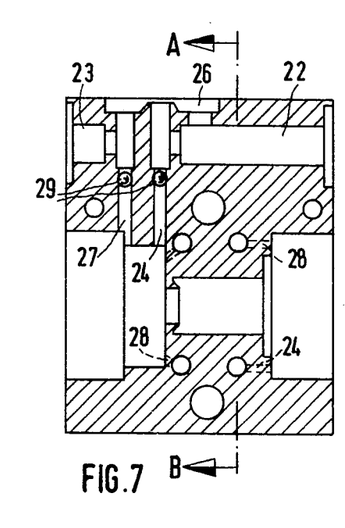
FIG. 7 is a cross sectional view generally corresponding to FIG. 3 of the basic body and showing finishing possibilities for adaptation to various control valve assemblies to be employed.
Figure 8:
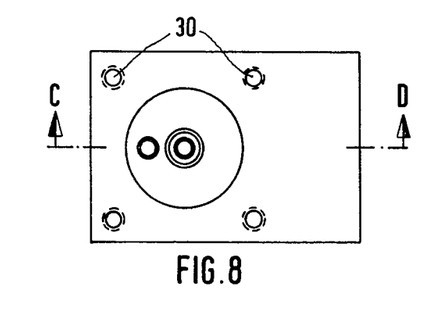
FIG. 8 is a top plan view of FIG. 7.
Figure 9:
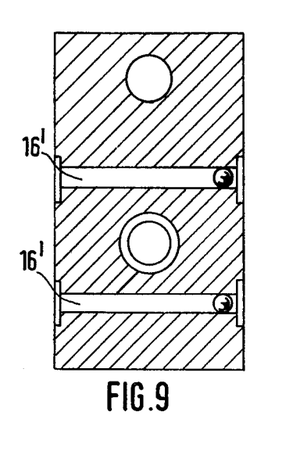
FIG. 9 is a cross section taken along the line A-B of FIG. 7.
Figure 10:
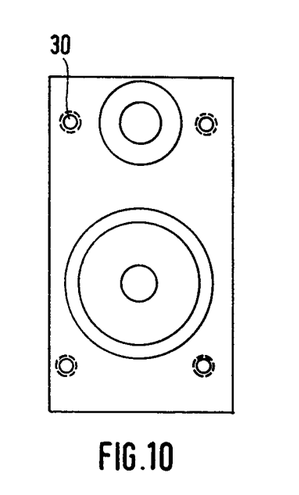
FIG. 10 is a view taken along the line C-D of FIG. 8.

Each of the control valve assemblies I–V has an identical basic body element with external tri-rectangular trihedral dimensions, i.e. each module has three functional areas as shown in detail in FIGS. 3–6. Parallel to the direction of the horizontal Z-axis (in FIG. 3 perpendicular to the plane of the drawing) there are provided in basic body 8 two straight through-holes 9 for longitudinal tie rods 35 (FIG. 2) extending throughout the length of the overall system. In FIG. 3 the Y-axis, through whose intersection point the vertical axis passes as X-axis, runs in the plane of the drawing at right angles to the Z-axis. In basic body 8 certain channel sections 10–15 are arranged in pairs, symmetrical to the X, Z-planes to form supply and control conduits. Said channel sections 10–15 form no through-holes, but (see FIG. 5) two-sided blind holes separated from one another by partition wall 16. Suitable annular zones 17 are provided on the ports of channel sections 10–15 for the insertion of sealants.

Perpendicular to the X, Z-planes in the direction of the Y-axis there is worked into basic body 8 a cross chamber 18 extending therethrough, having valve seat 19 and cylindrical sections 20, 21 of various diameters. Cross channel sections 22, 23 are provided parallel to cross chamber 18, the ports of said cross channel sections 23, 23 being usable as junction points. Cross chamber 18 communicates with vertical through-hole 24 which enters into valve seat 25 in the upper front side of basic body 8. Valve seat 25 is in communication with another vertical through-hole 27 via annular channel 26.

Basic body 8 of FIGS. 3–6 can be adapted to the widest possible range of applications with different valve functions by simple finishing processes, such as eliminating partition walls 16, shutting off channels or through-holes by pressing balls thereinto and drilling connecting holes as taps for existing channels. For example, as shown in FIGS. 7–10, additional bore holes 28 may be provided between channel sections and annular spaces. Individual partition walls 16 may be pierced, as shown at 16' in FIG. 9. Finally, bore holes can be made between cross-channel sections 22, 23 and annular channel 26 or through-holes 24, 27. Also, each of through-holes 24, 27 or both can be shut off by pressing balls 29 thereinto.

In the faces of basic body 8 pierced by the Z-axis, threaded bore holes 30 can be made to fasten cover plates 40, as will be described hereinafter.

As a rule, in each of a plurality of basic bodies 8 which are set in a row, channel section 10 is used for compressed air and channel section 14 for water. Compressed air can be fed to one side of valve seat 19 (see 36 in FIG. 11) by connecting channel section 10 with cylindrical section 20. If compressed air must be fed to the opposite side of valve seat 19 for another valve function, basic body 8 can be rotated 180° about vertical axis X, which is an axis of symmetry for this purpose, so that channel section 11 is in alignment with channel section 10 and channel section 15 is in alignment with channel section 14 of an adjacent basic body. In this way, different valve functions can be realized because of the arrangement of the longitudinal channel sections which are symmetrical to the vertical X-axis and extend throughout the length of the Z-axis.

Figure 1:
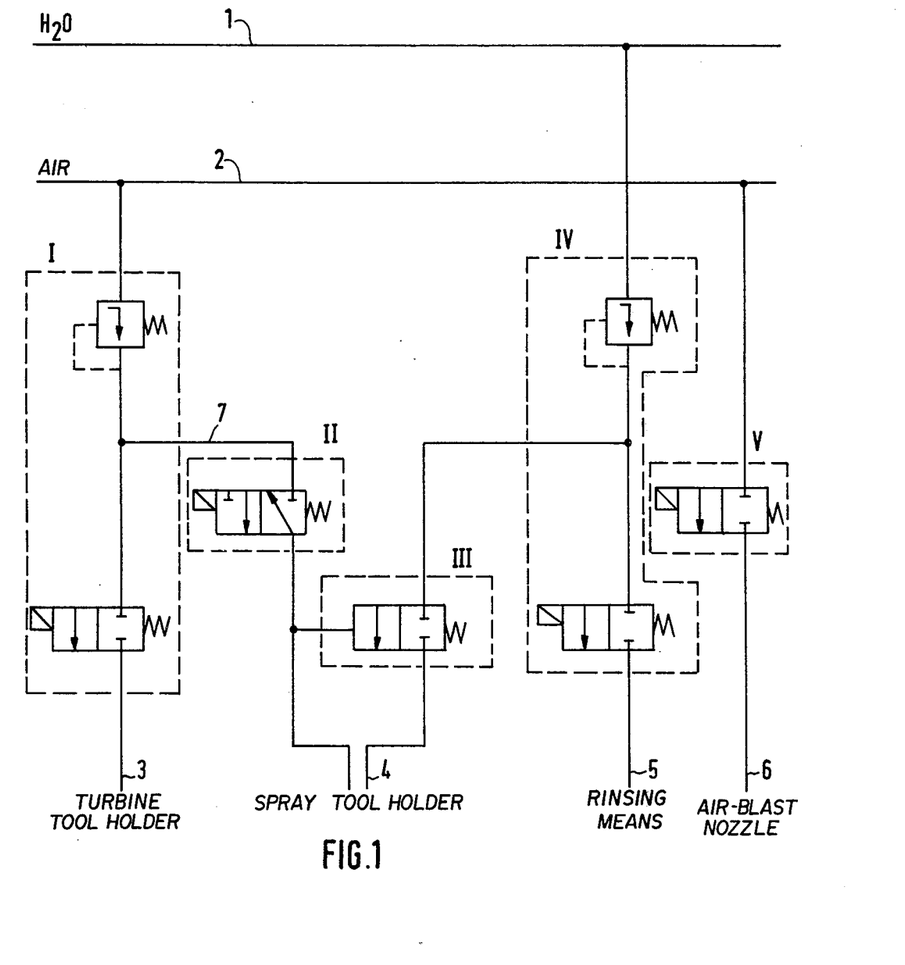
FIG. 1 shows schematically a diagram of a control valve arrangement embodying the principles of the invention with valve assemblies I-V.

The realization of a variety of valve functions will be discussed hereinafter with reference to the device shown in FIGS. 1 and 2 in conjunction with FIGS. 11–15. As shown in FIG. 2, there are attached to the free front ends of the basic bodies of control valves I and V a connecting end plate 31 and a terminating end plate 32. End plate 31 has connecting channel 33 for compressed-air conduit 1 and connecting channel 34 for water conduit 2. Connecting channels 33 and 34 are inclined 90° inside end plate 31 and enter into channel sections 10 or 14 of control valve block I. When control valve assemblies I–V are arranged side by side throughout the length of the Z-axis (except in II which, in the example described, is rotated 180° about the X-axis in the manner described earlier) channel sections 10 and 14, properly aligned, enter into communication with one another, so that compressed air and water under pressure are fed simultaneously through the channels formed by the sections to all the control valve assemblies, provided partition walls 16 have been removed. Longitudinal tie rods 35 (shown schematically in FIG. 2) extend across through-holes 9, the valve assemblies being clamped together with said tie rods 35 to form a compact entity. Tie rods 35 also extend across corresponding through-holes 9' of end plates 31 and 32 and carry at the ends thereof a head or a thread section for nuts.

Control valve I (FIG. 11) comprises a pressure regulator valve in cross chamber 18 and also a 2/2 directional-control valve having valve seat 25. Here, basic body 8 is finished as follows: Channel section 10 for compressed air is connected by tap hole 36 with chamber section 20. Similarly, channel section 11 is connected by tap hole 37 with chamber space 38 behind valve seat 19. Through-hole 27 is shut off by ball 29 pressed thereinto. Annular channel 26 is connected by bore hole 39 with cross channel 22.

Figure 11:
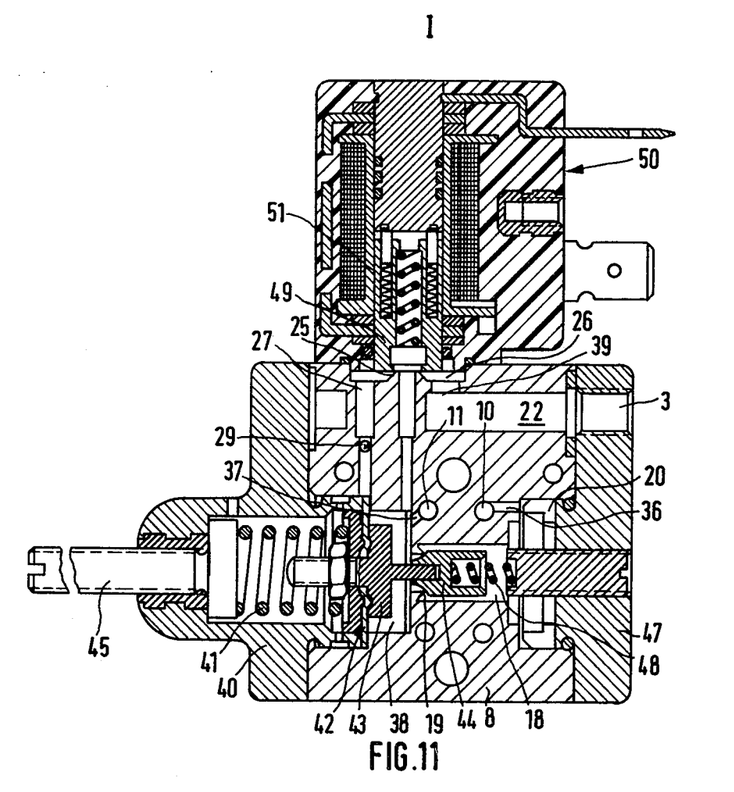
FIGS. 11-15 are cross sectional views of valves I-V of the device shown in FIG. 1.
Figure 12:
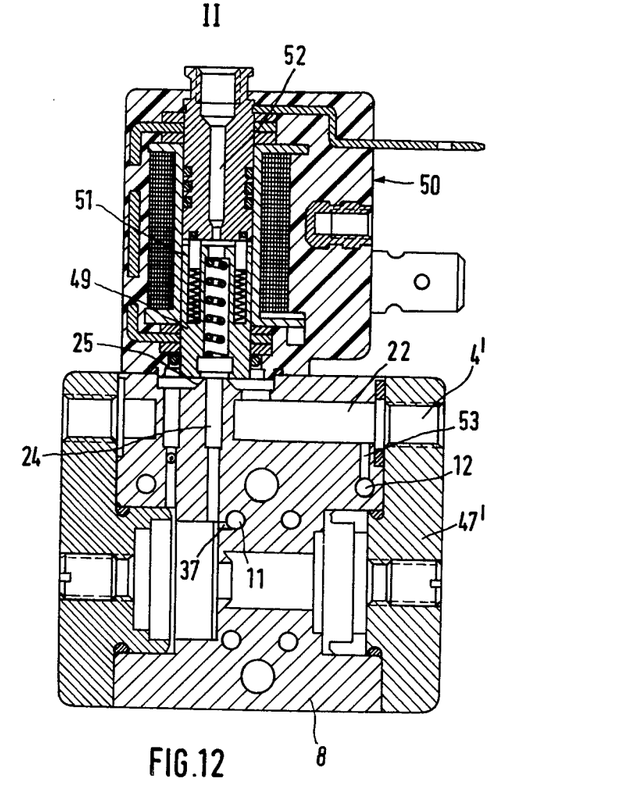

Basic body 8 of control valve I is equipped with fitting cover 40 containing diaphragm 42 tensioned by spring 41. Diaphragm 42, in turn, is connected via piston 43 with valve body 44 coacting with valve seat 19.

Adjusting screw 45 serves to adjust the initial tension of spring 41 and, thereby, to adjust the control pressure. Chamber section 20 is likewise shut off by cover plate 47 containing adjustable stop means 48 for valve body 44.

Valve body 49 of magnet arrangement 50 coacts with valve seat 25. Valve chamber 51 for valve body 49 is completely sealed off. Said valve acts as a 2/2 directional-control valve for cross channel 22 which leads to junction point 3 in cover plate 47.

Normally, spring 41 holds valve body 44 in the open position. As soon as the pressure on the outlet side of valve seat 19 in chamber space 38 rises to the adjusted control pressure, said pressure regulator valve is closed, because valve body 44 engages valve seat 19, with the result that inside chamber 38 the compressed air is at all times under the adjusted control pressure. Valve body 49 is controlled by means of magnet arrangement 50 and releases the path for said compressed air to junction point 3 for the turbine. Further, the compressed air is conducted under the control pressure to channel section 11 via bore hole 37, said channel section 11 being in communication with channel section 11 of valve assembly II.

Valve assembly II (FIG. 2) operates as a 3/2 directional-control valve.

Pressure-controlled air is introduced into basic body 8 via channel section 11 and reaches valve seat 25 through tap hole 37 and through-hole 24. Valve seat 25 is shut off by valve body 49 of magnet assembly 50. Valve chamber 51 is equipped with ventilation hole 52 (see FIG. 12), so that cross channel 22 is ventilated in the switching condition of the valve arrangement shown in the drawing. Cross channel 22 is connected to junction point 4' in cover plate 47'. Junction point 4' leads to the air connection of the spray tool holder. Bore hole 53 in cross channel 22 branches off to channel section 12. Channel section 12 conducts compressed air as a control medium to pilot-operated valve assembly III operating as a check valve. The operation of valve assembly II working as a control valve is apparent from FIG. 12.

Figure 13:
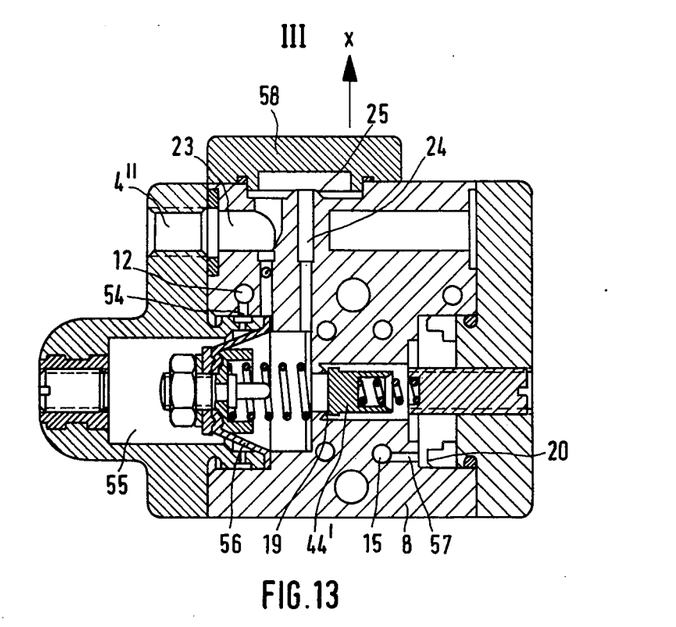
Figure 14:
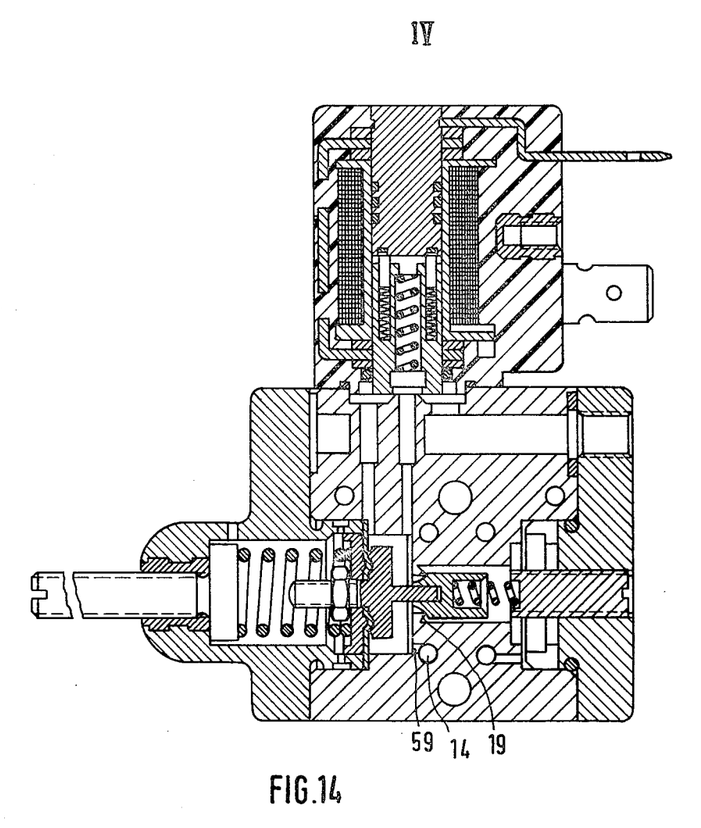

Basic body 8 of valve assembly III (FIG. 13) operating as a check valve is rotated 180° about the X-axis in relation to the position of the basic bodies of valve assemblies I and II, so that pressure-controlled water can be supplied from valve assembly IV working as a control valve via channel section 15 (FIG. 14).

Pressure-controlled air is supplied to the control valve in valve assembly III via channel section 12 and is fed via bore hole 54 to pilot-operated chamber 55 formed in cover plate 40. Control diaphragm 56 is operatively connected with valve body 44' via connecting links. The pressure-controlled water flows from channel section 15 via bore hole 57 to chamber section 20 in front of valve seat 19.

When valve body 44' is in the open condition, the water under pressure can flow via channel section 25 into cross channel 23 to junction point 4'' provided in cover 40. In this case, valve seat 25 is bridged by cover cap 58. Thereby, control valve assembly III transmits pressure-controlled water for the spray tool holder; it is pilot-operated by the compressed air.

The valve assembly operating as a control valve and supplying pressure-controlled water for the spray tool holder and also for the rinsing means connected to junction point 5 is substantially similar to control valve assembly I. It comprises a control valve and a 2/2 directional-control valve operating as a shutoff valve.

The outlet side of valve seat 19 is connected via tap hole 59 (FIG. 14) with channel section 14 which, in turn, is aligned with channel section 14 of control valve assembly III (FIG. 13), because the latter is placed between valve assemblies II and IV in a position rotated 180° about the X-axis.

Figure 15:
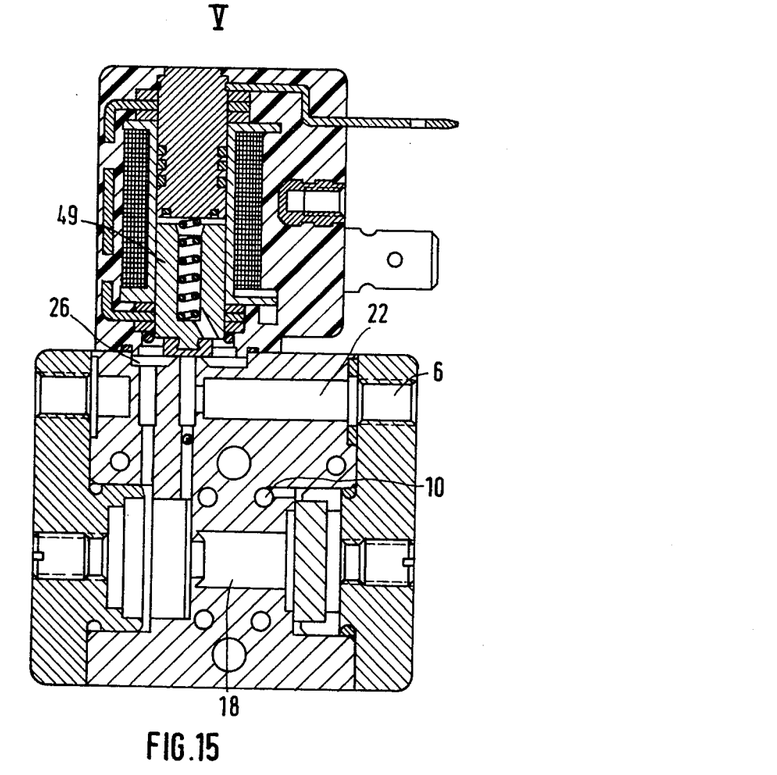

Finally, channel section 10 of valve assembly V is connected directly to compressed-air conduit 1. The compressed air reaches annular channel 26 via cross chamber 18. Valve body 49 works as a shutoff valve and controls the through-hole to cross channel 22, which is in communication with junction point 6 for the air-blast nozzle.

The above detailed description of the cross sections illustrated in FIGS. 11-15 shows that there are employed in the individual valve assemblies basic bodies that are adapted to the various fields of application by supplementary bore holes and/or by pressing shutoff balls thereinto, by selecting one of two possible angular positions rotated 180° in relation to each other, and by eliminating partition walls which are provided in the basic body in its initial stare.

Figure 16:
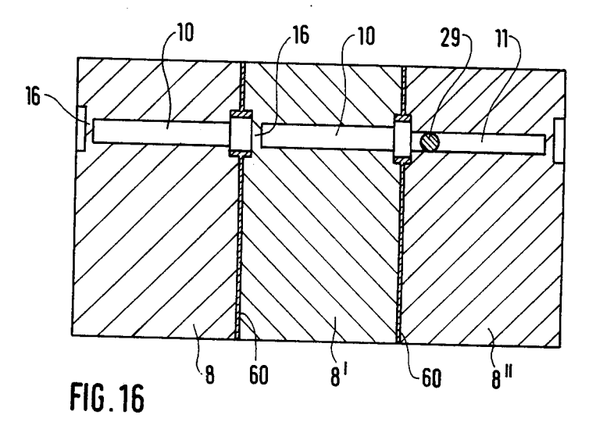
FIG. 16 is a cross sectional diagrammatic view of the capability of control channels to be assembled into connected control valve assemblies.

These adaptation possibilities are shown in FIG. 16, where partition wall 16 of channel sections still exists in basic bodies 8, 8', 8''. Basic body 8'' is rotated 180° about the X-axis, so that channel section 10 of basic body 8' is properly aligned with channel section 11 of basic body 8''. Channel section 11 of basic body 8'' is shut off on its left end (FIG. 16) by pressing ball 29 thereinto.

Figure 17:
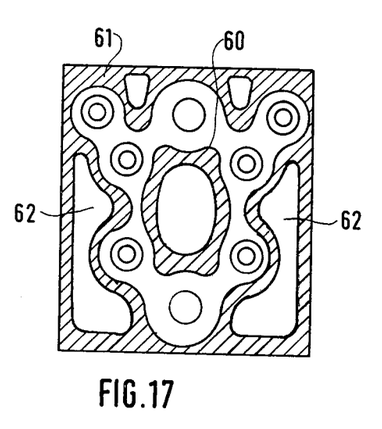
FIG. 17 is a sectional view of a sealant member.
Figure 18:
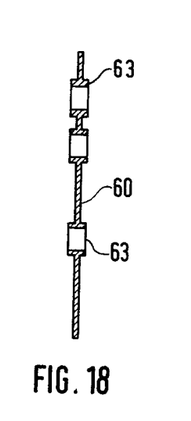
FIG. 18 is a side elevational view of FIG. 17.

Sealants 60 are provided between the abutting front sides of basic bodies 8 of valve assemblies I-V which are ranged side by side (FIGS. 17 and 18). The hatched area 61 lies on the front sides of basic body 8. To facilitate injection molding, cavities are provided within the extents of area 62. Sealant 60 forms seal-ring-type cylindrical connectors 63 which protrude from its surface and seal off corresponding annular zones 17 of the ports of the channel sections against one another when the valve assemblies are clamped together by means of longitudinal tie rods 35.

The example described hereinabove permits numerous modifications, such as adding further valve assemblies for supplementary connections. Frequently, two connections must be provided for turbine tool holders whose turbines must be acted upon by water controlled under varying pressures. In this case, valve assembly I of the example described hereinabove would also have to be preceded or followed by a substantially similar valve assembly.

What is claimed and desired to be secured by Letters Patent of the United States is:

1. A control valve arrangement for dental equipment, wherein at least two modular type control valve assemblies having at least three functional zones are combined into a control group disposed between end closure elements and arranged to be clamped to form an entity, wherein aid modules are clamped together in one direction by longitudinal tie rods and have channels for control and supply media made up of channel sections having ports which are joined together, said channels arranged to extend in said one direction of said modules, further wherein said modules comprise substantially identical bodies having at least two sides with said ports disposed in said sides, which are arranged to be clamped together with each said module having said ports arranged symmetrically to a normal central plane (ZX)

which extends in said one direction of clamping, each said module further being provided with a cross chamber terminating in a valve seat, said cross chamber having a geometrical axis (Y) which extends perpendicular to said one direction of clamping of said modules and is intersected at an intersection point at right angles by a central geometrical vertical axis (x) of said module, said module including a third geometrical axis (z) passing through said intersection point and extending at right angles to said geometrical axis (y) and said vertical axis (x), and that in the interior of each module there are provided further channel sections which extend between the ports disposed in said sides.

2. The control valve arrangement as set forth in claim 1, further wherein four of said further channels lie in pairs symmetrically to said vertical axis (X) as well as to said axis (Y) of said cross chamber and two of said further channels lie symmetrically only to said vertical axis (X).

3. The control valve arrangement as set forth in claim 1, further wherein in addition to said cross chamber there are provided cross channel sections which extend parallel to said cross chamber and each are properly aligned with the other.

4. The central valve arrangement as set forth in claim 1, further wherein said modules are also traversed, in said normal central plane (ZX) which extends in the direction of clamping, by through-holes arranged to receive a pair of longitudinal tie rods and said through-holes being separated an equal distance from said intersection point.

5. The control valve arrangement as set forth in claim 1, further wherein said channel sections have readily removable partition walls.

6. The arrangement as set forth in claim 1, further wherein said cross chamber communicates with a through-hole that terminates in a valve seat.

7. The control valve arrangment as set forth in claim 1, further wherein said functional zones of said modules are provided with cover plates, said cover plates further including means for coaction with one or more valve seats and channels in said module.

8. The control valve arrangement as set forth in one claim 1, further wherein predetermined ones of said channel sections in said modules are provided with ball means to control flow therethrough.

9. The control valve arrangement as set forth in claim 1, further wherein a seal means is interposed between each said module to permit supply media to flow therebetween.

10. The control arrangement as set forth in claim 9, further wherein said seal means includes integral grommet means for cooperation with respective ports of said channel sections.

* * * * *